(12) United States Patent
Marcellus

(10) Patent No.: US 8,118,509 B2
(45) Date of Patent: Feb. 21, 2012

(54) AUTOMATIC SUBSTANCE APPLICATOR SYSTEM

(76) Inventor: Dianna Marcellus, Hyde Park, MA (US)

( * ) Notice: Subject to any disclaimer, the term of this patent is extended or adjusted under 35 U.S.C. 154(b) by 1318 days.

(21) Appl. No.: 11/744,940

(22) Filed: May 7, 2007

(65) Prior Publication Data

US 2007/0269255 A1 Nov. 22, 2007

Related U.S. Application Data

(60) Provisional application No. 60/798,637, filed on May 8, 2006.

(51) Int. Cl.
*A46B 11/02* (2006.01)
*B43K 5/02* (2006.01)

(52) U.S. Cl. ........ 401/188 R; 401/187; 604/65; 604/67; 604/151

(58) Field of Classification Search .................. 401/187, 401/188 R; 604/65, 67, 93.01, 151; 128/DIG. 12
See application file for complete search history.

(56) References Cited

U.S. PATENT DOCUMENTS

| | | | | |
|---|---|---|---|---|
| 5,139,357 A * | 8/1992 | Reents | ...................... | 401/188 R |
| 5,628,731 A * | 5/1997 | Dodge et al. | ........... | 128/DIG. 12 |
| 6,200,289 B1 | 3/2001 | Hochman et al. | ................ | 604/67 |
| 6,656,162 B2 * | 12/2003 | Santini et al. | ............... | 604/93.01 |
| 6,749,587 B2 | 6/2004 | Flaherty | ........................ | 604/151 |
| 6,786,885 B2 | 9/2004 | Hochman et al. | ................ | 604/67 |
| 6,790,198 B1 * | 9/2004 | White et al. | ..................... | 604/151 |
| 6,887,216 B2 | 5/2005 | Hochman et al. | ................ | 604/67 |
| 6,945,954 B2 | 9/2005 | Hochman et al. | ................ | 604/67 |
| 7,169,135 B2 * | 1/2007 | Duchon et al. | .................. | 604/151 |
| 7,236,936 B2 * | 6/2007 | White et al. | ..................... | 604/151 |
| 7,645,258 B2 * | 1/2010 | White et al. | ..................... | 604/67 |
| 7,753,880 B2 * | 7/2010 | Malackowski | .................. | 604/65 |
| 7,806,852 B1 * | 10/2010 | Jurson | ............................ | 604/65 |
| 7,976,508 B2 * | 7/2011 | Hoag | ................................ | 604/67 |
| 8,025,634 B1 * | 9/2011 | Moubayed et al. | ............. | 604/65 |
| 2002/0016567 A1 | 2/2002 | Hochman et al. | ............. | 604/131 |
| 2002/0052574 A1 | 5/2002 | Hochman et al. | ............... | 604/31 |
| 2002/0169439 A1 | 11/2002 | Flaherty | ...................... | 604/891.1 |
| 2003/0078534 A1 | 4/2003 | Hochman et al. | ................ | 604/67 |
| 2006/0122555 A1 | 6/2006 | Hochman | ........................ | 604/67 |

FOREIGN PATENT DOCUMENTS

| WO | WO9302720 | 2/1993 |
|---|---|---|
| WO | WO02068015 | 9/2002 |
| WO | WO2004098682 | 11/2004 |
| WO | WO2004098683 | 11/2004 |

* cited by examiner

*Primary Examiner* — Tuan Nguyen

(74) *Attorney, Agent, or Firm* — Burns & Levinson LLP; Jerry Cohen; David W. Gomes

(57) ABSTRACT

This invention relates generally to assistive devices, and more particularly refers to an automatic substance applicator system for applying or administering a substance to a receiving surface.

3 Claims, 5 Drawing Sheets

AUTOMATIC SUBSTANCE APPLICATOR SYSTEM

CROSS REFERENCE TO RELATED APPLICATIONS

This application claims priority under 35 U.S.C. §119 from provisional application Ser. No. 60/798,637 entitled AUTOMATIC SUBSTANCE APPLICATOR SYSTEM, filed on May 8, 2006.

BACKGROUND

This invention relates generally to assistive devices, and more particularly to a device that can automatically apply a substance to a receiving surface under the control of the user or by remote control.

Applying a substance such as nail polish to a receiving surface such as a fingernail or a toenail can require the ability to evenly and uniformly distribute the substance to a variable-sized and variable-textured receiving surface. Applying a substance such as a drug to a receiving skin surface can additionally involve dosage timing. Such activities, when performed manually, can require steady and even movement, as well as a good memory, which can be difficult for users with, for example, shaky hands, poor eyesight, poor eye/hand coordination, and poor memories.

What is needed is a system that assists users in applying substances to receiving surfaces with a uniform and steady motion. Still further, what is needed is a system that assists users with dosage timing.

SUMMARY

The present invention is an automatic substance applicator system that can be used to apply a predetermined amount of substance to a receiving surface in a steady and controlled way, optionally at pre-selected intervals. For example, the automatic substance applicator system could be used to automatically apply nail polish to fingernails, or drugs to a skin surface or subcutaneously. The automatic substance applicator system can include, but is not limited to, a controller having switches to control such features as, for example, power, pump speed, and applicator motor speed. The controller can optionally provide switches to control an identification means such as, for example, a biosensor, an adjustable dosage meter, and a timer. The pump can draw or push a substance from a reservoir and supply the substance to an applicator such as, for example, a brush, a sponge, a nozzle, or combinations thereof, possibly through tubing. The applicator can be connected to a positioning or alignment device, and actuator such as a servo motor, which can adjust the position of the applicator, thereby automatically distributing the substance across the receiving surface. The biosensor or identification means can determine the identity of the person to whom the substance will be applied, the timer can provide the substance at pre-selected intervals, and the dosage meter can provide a pre-determined amount of substance. The applicator system can include an applicator that is removable to accommodate a variety of different applicator head shapes, sizes, and uses.

The controller can optionally have an electronic connection, wired or wireless, that allows remote control of dosage amount and timing. For example, medical personnel could establish the dosage and timing through an internet connection and the controller could automatically adjust its parameters according to the instructions from the medical personnel. The user could be informed of any external interaction with medical personnel through a wired or wireless personal device, for example, a Personal Data Assistant (PDA), a Personal Computer (PC), or a display associated with the controller or actuator. Additionally, the controller could be geographically separate from the applicator and could send and receive wireless electronic signals to control the pump and actuator and to send/receive signals to/from the identification means. The controller can include sensors including, but not limited to, for example, a position sensor, an angle sensor, and a pump sensor.

For a better understanding of the present invention, together with other and further objects thereof, reference is made to the accompanying drawings and detailed description. The scope of the present invention is pointed out in the appended claims.

DETAILED DESCRIPTION

Embodiments according to the present teachings are now described more fully hereinafter with reference to the accompanying drawings. The following configuration description is presented for illustrative purposes only.

Figure 1A:
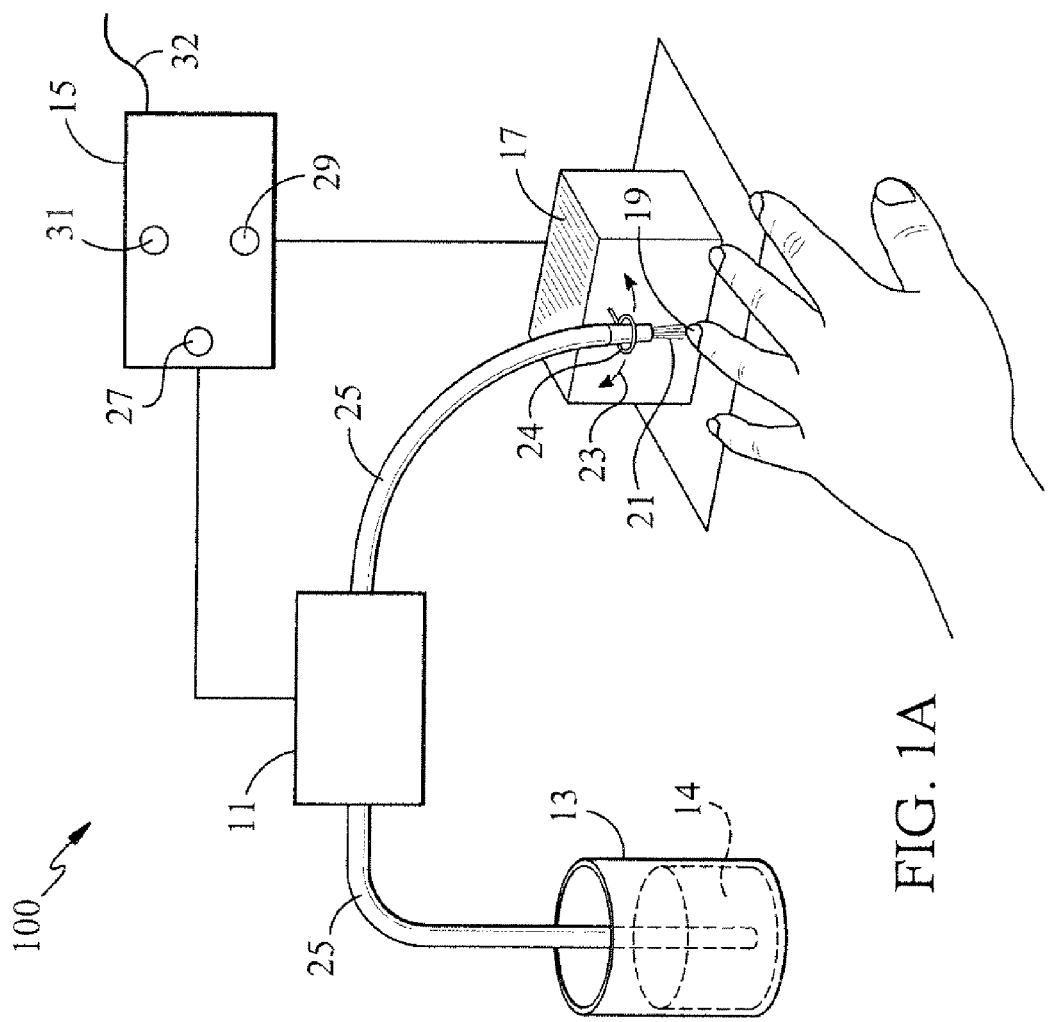
FIG. 1A is a schematic diagram of an illustrative embodiment of the system of the invention in which a substance, possibly fingernail polish, is being applied to fingernails.

Referring now to FIG. 1A, applicator system 100, an illustrative embodiment according to the present teachings, can include, but is not limited to, reservoir 13 holding substance 14, pump 11 coupled with reservoir 13, tube 25 coupled with pump 11, applicator 21 coupled with tube 25, and actuator 17 coupled with application 21. Pump 11 can draw substance 14 from reservoir 13 and, if tube 25 is present, provide substance 14 received from pump 11 to tube 25. Applicator 21 can receive substance 14 from tube 25, if present, and place substance 14 onto receiving surface 19. Actuator 17 and motion coupler 24 can move applicator 21 to distribute substance 14 over receiving surface 19. Applicator system 100 can include controller 15 that can control pump 11 and actuator 17, as well as sense the status of devices under the control of controller 15, and provide an on/off switch 31 and/or a power cable 32 or battery (not shown). Applicator system 100 could be wirelessly controlled. Substance 14 can be, for example, nail polish or nail polish remover, and receiving surface 19 can be. for example, a fingernail or toenail.

Continuing to refer to FIG. 1A, a method for operating of the device of the present teachings can include the steps of pumping substance 14 from reservoir 13 to applicator 21, activating actuator 17 that is coupled with applicator 21, and applying substance 14 across receiving surface 19, for example, in a Cartesian space 23, or any other Cartesian shape, through applicator 21 driven by actuator 17. The method can further include the steps of setting the speed of actuator 17 to control distribution of substance 14 across receiving surface 19, fixedly positioning receiving surface 19 with respect to applicator 21, coupling pump 11 to applicator 21 by means of tube 25, mounting tube 25 to position applicator 21 to distribute substance 14 across receiving surface 19, moving, for example, rotating, applicator 21, for example, in Cartesian space 23, or moving laterally, to distribute substance 14 across receiving surface 19, and adding substance 14 to reservoir 13.

Figure 1B:
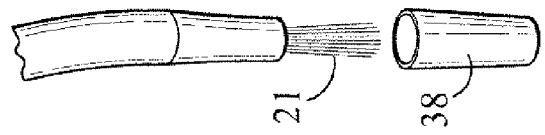
FIG. 1B is a schematic diagram of the applicator cap of the present invention.

Referring now to FIG. 1B, applicator 21 can be protected by cap 38.

Figure 1C:
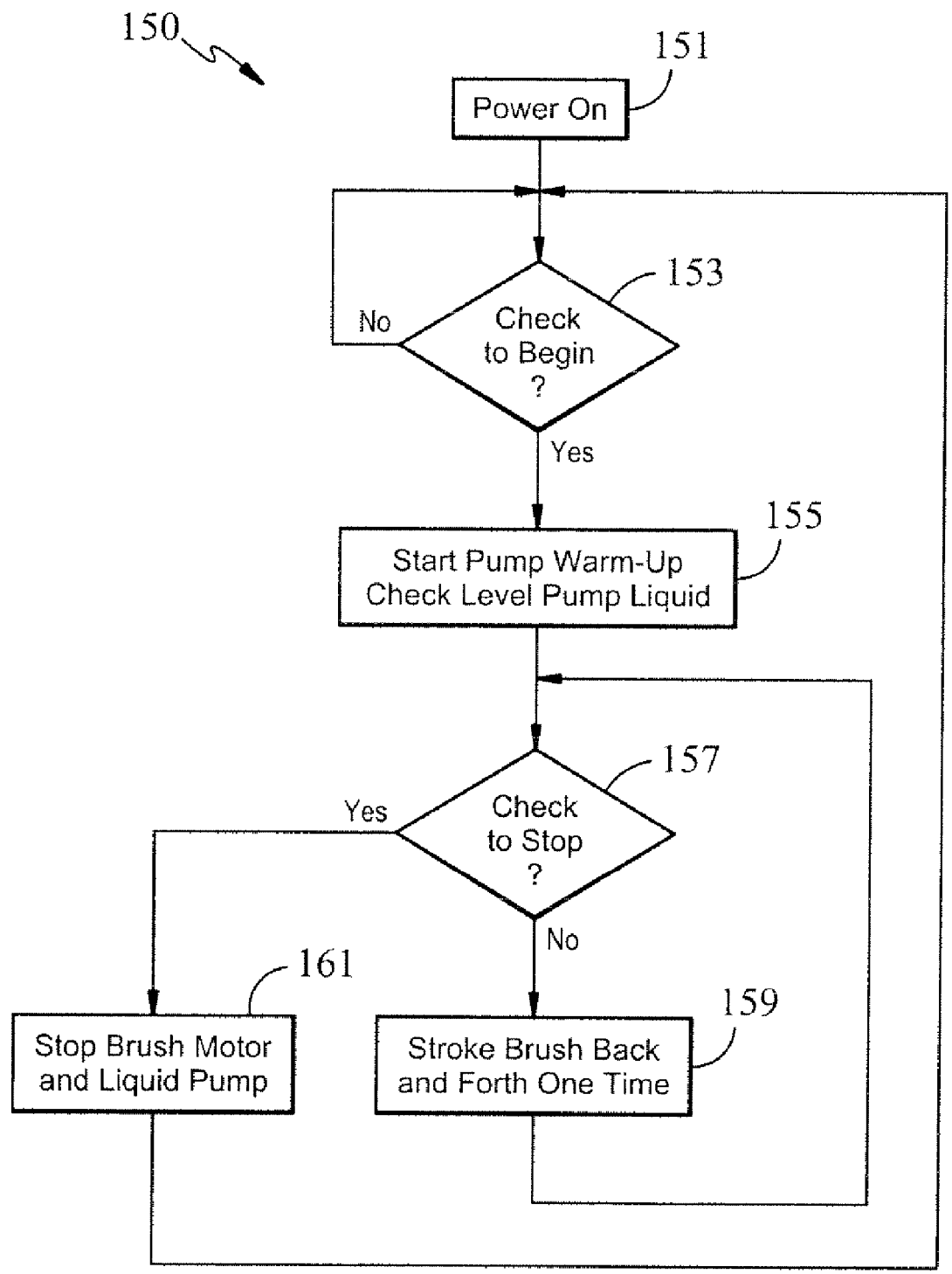
FIG. 1C is a flowchart of the method of operation of an illustrative embodiment of the invention.

Referring now primarily to FIG. 1C, method 150 (FIG. 1C) for automatically applying substance 14 (FIG. 1A) to a receiving surface 19 (FIG. 1A) can include the steps of powering on 151 (FIG. 1C) applicator system 100 (FIG. 1A) with on/off switch 31 (FIG. 1A) and, if begin checks such as, for example, checking 153 (FIG. 1C) if there is substance 14 in reservoir 13 and checking 153 (FIG. 1C) if receiving surface 19 is in the proper location, are unsuccessful, return to step 153. Possible actions if the checks are unsuccessful can include, but are not limited to including, presenting warnings to the user such as "NO NAIL POLISH" or "PLEASE PLACE FINGER IN POLISH STATION". If begin checks are successful, method 150 (FIG. 1C) can include the steps of starting 155 (FIG. 1C) pump 11, warming up 155 pump 1, pumping 155 (FIG. 1C) substance 14 to tube 25 (FIG. 1A), and checking 155 level of substance 14 in reservoir 13. When a start button is depressed and before a stop button is depressed, method 150 (FIG. 1C) can include the steps of enabling actuator 17 (FIG. 1A) to swing 159 (FIG. 1C) applicator 21 (FIG. 1A), for example, left and right at, for example, 0.25 second period to apply substance 14 (FIG. 1A) to receiving surface 19 (FIG. 1A), and returning to step 157. If the stop button is depressed, method 150 (FIG. 1C) can include the steps of stopping 161 (FIG. 1C) actuator 17 (FIG. 1A), which stops applicator 21 (FIG. 1A) and pump 11 (FIG. 1A), and returning to step 153. Other possible actions when the stop button or on/off switch 31 is depressed can include, but are not limited to including, powering off applicator system 100 if on/off switch 31 is depressed, or stopping actuator 17 if the stop button is depressed, then powering off applicator system 100, returning to step 151.

Figure 2B:
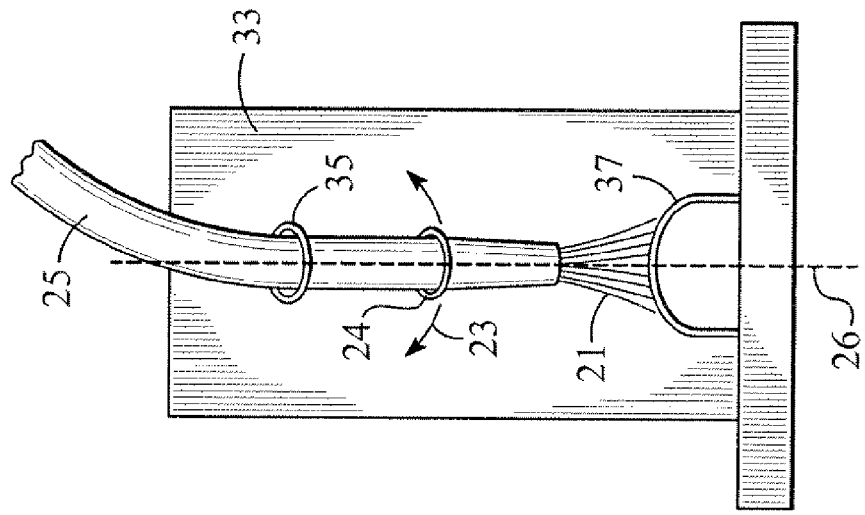
FIG. 2B is a schematic diagram showing a front view of the applicator distribution of the invention.
Figure 2A:
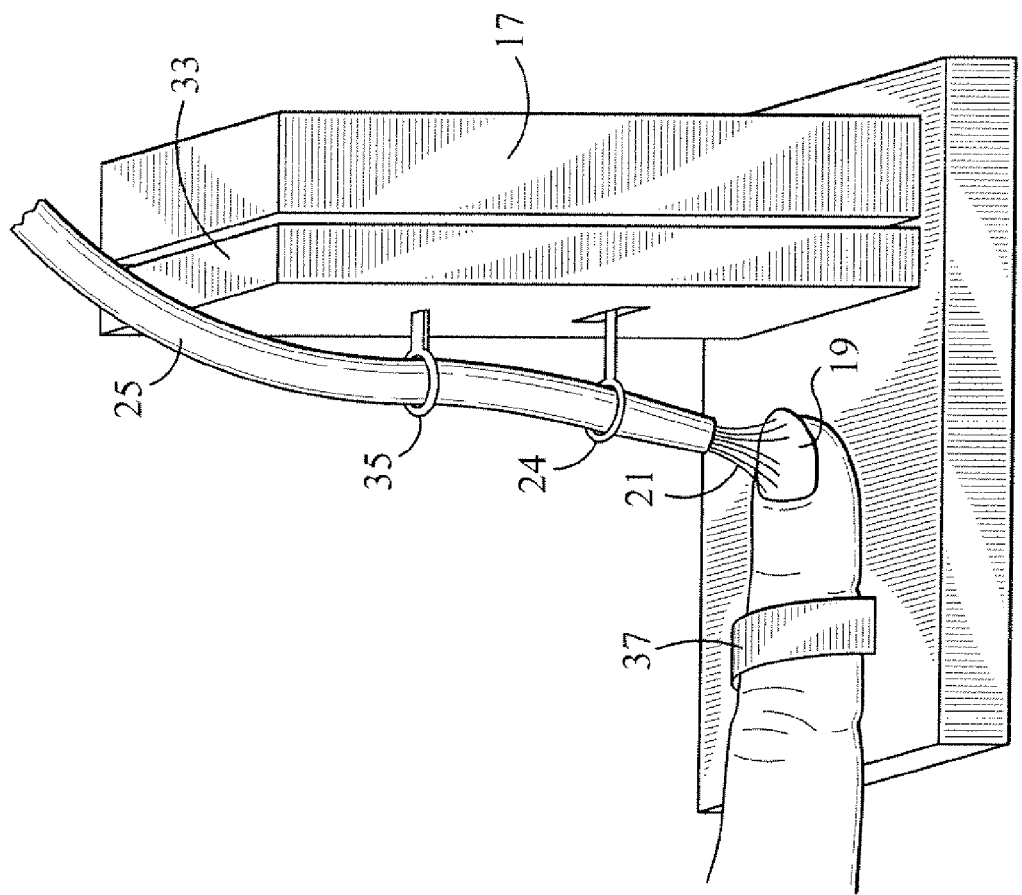
FIG. 2A is a schematic diagram of the applicator holder and stabilizer of an illustrative embodiment of the invention.
Figure 2C:
FIG. 2C is a schematic diagram of an applicator for removing nail polish.
Figure 2D:
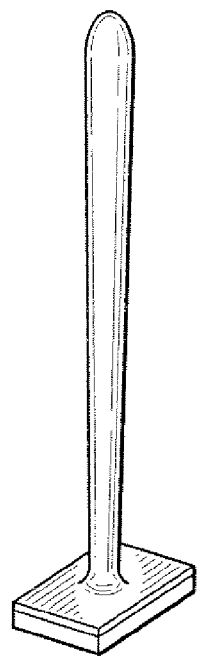
FIG. 2D is a schematic diagram of an applicator for applying a nail polish stamp.
Figure 2E:
FIG. 2E is a schematic diagram of a French tip nail polish applicator.

Referring now primarily to FIGS. 2A and 2B, tube 25 can be fixedly positioned by holder 33 and stabilizer 35, and receiving surface positioner 37 can maintain receiving surface 19 (FIG. 2A) in a fixed position while applicator 21 distributes substance 14 (FIG. 1A). Actuator 17 (FIG. 2A) can move applicator 21 across, for example, a Cartesian space 23 (FIG. 2B) to cover a pre-selected area of receiving surface 19. Actuator 17 can operate at a plurality of speeds controlled by controller 15 (FIG. 1A) which can cause applicator 21 to move in a swinging motion, in the illustrative embodiment, taking, for example, a few seconds for a complete cycle when a fingernail is receiving surface 19. Applicator 21 can, for example, move a pre-selected distance from neutral position (26), for example, up to ¼ turn right and ¼ turn left of neutral position 26 (FIG. 2B) of applicator 21, by means of actuator 17 and motion coupler 24. Applicator 21 can also move laterally, or can remain in situ while drawing patterns composed of, for example, dots. Applicator 21 can be removed and replaced by applicators depicted in FIGS. 2C, 2D, and 2E, for example. In FIG. 2C is shown a sponge-like brush for removing nail polish, for example. In FIG. 2D is a shown a designer brush that could be used to stamp on a design such as a star, rose, etc. In FIG. 2E is shown a thin brush to create, for example, a French tip.

Figure 3:
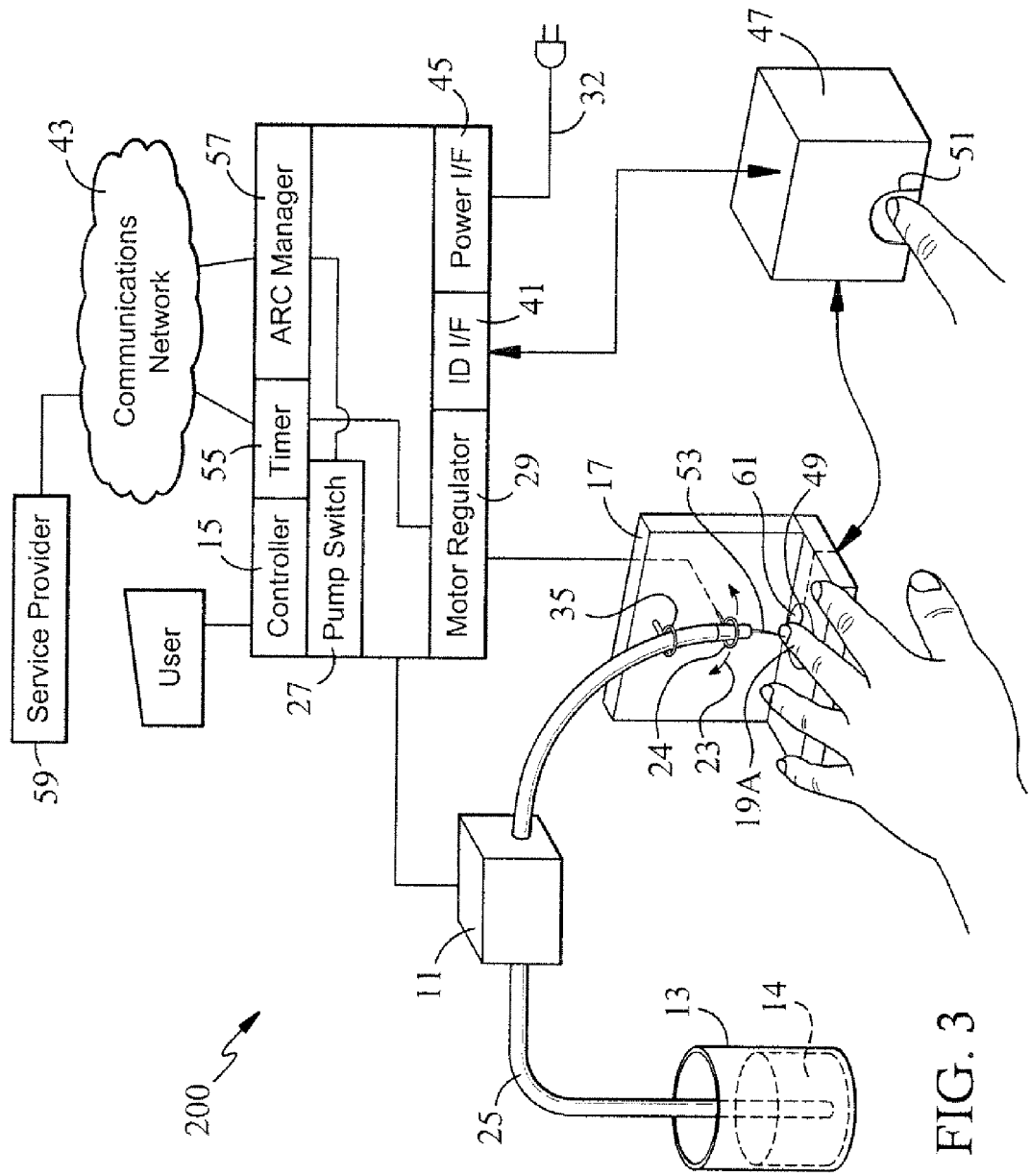
FIG. 3 is a schematic diagram of an illustrative embodiment of the system of the invention in which the substance, possibly a medication, is being applied to skin subcutaneously.

Referring now to FIG. 3, medical system 200, another embodiment of the present teachings, the embodiment illustrating subcutaneous dose administration, can include, but is not limited to, the elements of applicator system 100 (FIG. 1A), as well as medical applicator 53, identification database 47, and identification reader 51. A method for using medical system 200 can include, but is not limited to, the step of receiving identifying information, such as a fingerprint, to identification reader 51 to initialize identification database 47. Identification database 47 can be electronically coupled with controller 15 through identification interface 41, which can receive signals from identification database 47 through, for example, a medium such as, for example, wired or wireless technology. The method of use of medical system 200 can further include the step of providing power through power interface 45 to controller 15. Controller 15 can, for example, be battery-operated, can have a wall connection through electric cord 32, or can be powered by another method, and can be wirelessly controlled. The method can further include the steps of receiving an identifying surface 49, shown illustratively as the side of receiver 19A that is flush with sensor platform 61, reading identifying information from identifying surface 49 through identification reader 51, and comparing the received identifying information with identifying information stored in identification database 47 during the previous initialization step. If there is a match, the method can include the step of providing, by identification database 47, a signal to controller 15 through identification interface 41. If there is no match, controller 15 can, for example, take no activation action with respect to pump 11 and actuator 17. Note that identification database 47 and sensor platform 61 can be integrated devices or can be physically and/or electronically separated and can, for example, communicate through wired, wirelessly, or an internet connection. The configuration shown in FIG. 3 is illustrative.

Continuing to refer to FIG. 3, if controller 15 receives an activation signal from identification database 47, the method can include the step of sending, by controller 15, a timer signal to initialize timer 55 and set a time for administering a dosage to receiver 19A associated with the identifying information. When timer 55 determines that, for example, a pre-selected timing interval has expired, the method can include the step of sending, by timer 55, a pump signal to pump switch 27 to activate pump 11, and a regulator signal to motor regulator 29 to activate actuator 17. The method can also include the steps of receiving, from movement manager 57, and sending to motor regulator 29, a dosage location with respect to receiver 19A. Movement manager 57 can receive the dosage location from, for example, service provider 59 through, for example, a local graphical user interface (not shown) or a remote user interface or automatic means through communications network 43, or the dosage location can be associated with the identifying information, or any other appropriate means to determine dosage location. For example, if the dosage is to be spread across the skin, movement manager 57 can provide the geometric parameters. As another example, as shown in FIG. 3, if the dosage is to be administered in a single location, movement manager 57 can provide that single location to motor regulator 29.

Continuing to further refer to FIG. 3, the method can further include the steps of positioning medical applicator 53 with respect to receiver 19A according to a positioning signal from movement manager 57, and activating actuator 17 to properly position medical applicator 53. The method can still further include the step of pumping substance 14 from substance reservoir 13 through tube 25 to medical applicator 53 while actuator 17 positions medical applicator 53, if necessary, appropriately for administering the dosage. The method can even still further include the step of discontinuing the dosage when a signal is received from timer 55, where timer 55 has associated, for example, a dosage time or dosage amount with the identifying information, the medication being administered, or any other appropriate means. In medical system 200, values such as dosage amount and applicator position can be established either locally to medical system 200, for example, through a touch pad, a computer, or any other means, or remotely, for example, through communications network 43, a Personal Data Assistant, a cell phone, or any other means. Further, the values can be established automatically through software executing in any of the components of medical system 200, or through user entry to a graphical user interface (not shown), either locally or remotely to medical system 200.

Although the invention has been described with respect to various embodiments, it should be realized that this invention is also capable of a wide variety of further and other embodiments. The following claims define the scope of the invention.

What is claimed is:

1. A medical system for delivering medication comprising:
   a reservoir configured to hold a substance;
   a pump coupled with said reservoir, said pump configured to draw said substance from said reservoir;
   a tube coupled with said pump, said tube configured to receive said substance from said pump;
   a medical applicator coupled with said tube, said medical applicator configured to receive said substance from said tube, and configured to administer said substance to a receiver;
   an actuator coupled with said medical applicator, said actuator configured to position said medical applicator with respect to the receiver; and
   an identification reader configured to receive identifying information associated with the receiver;
   wherein said identifying information is configured to enable startup of said actuator and said pump; and
   wherein said actuator and said pump are configured to deliver said medication through said tube and said medical applicator.

2. The medical system of claim 1 further comprising:
   an identification database configured to:
      receive, store, and compare said identifying information; and
      provide an activation signal to a controller based on said identifying information if said identifying information matches stored information in said identification database; and
   a timer configured to:
      receive a timer signal from said controller to initialize said timer for dosage administration;
      provide a pump signal to said pump switch to activate said pump; and
      provide a regulator signal to a motor regulator to activate said actuator.

3. The medical system as in claim 2 further comprising:
   a movement manager configured to:
      provide a dosage location to said motor regulator; and
      receive said dosage location from a service provider.

* * * * *